(12) United States Patent
Ravikumar et al.

(10) Patent No.: US 12,325,634 B2
(45) Date of Patent: Jun. 10, 2025

(54) PRODUCTION OF AMMONIA, METHANOL, AND SYNTHESIS PRODUCTS FROM ONE OR MORE GASIFICATION PRODUCTS

(71) Applicant: Fluor Technologies Corporation, Irving, TX (US)

(72) Inventors: Ravi Ravikumar, Lancaster, CA (US); Sunil Singhal, Gurugram (IN); Soumya Jyoti Choudhury, Faridabad (IN); Kakul Singh, Ghaziabad (IN)

(73) Assignee: Fluor Technologies Corporation, Irving, TX (US)

( * ) Notice: Subject to any disclaimer, the term of this patent is extended or adjusted under 35 U.S.C. 154(b) by 361 days.

(21) Appl. No.: 17/725,296

(22) Filed: Apr. 20, 2022

(65) Prior Publication Data

US 2022/0340419 A1 Oct. 27, 2022

Related U.S. Application Data

(60) Provisional application No. 63/179,023, filed on Apr. 23, 2021.

(51) Int. Cl.
*C01B 3/12* (2006.01)
*B01D 53/14* (2006.01)
(Continued)

(52) U.S. Cl.
CPC ............ *C01B 3/12* (2013.01); *B01D 53/1418* (2013.01); *B01D 53/1475* (2013.01);
(Continued)

(58) Field of Classification Search
CPC ... C01B 3/12; C01B 32/50; C01B 2203/0266; C01B 2203/0283; C01B 2203/0415;
(Continued)

(56) References Cited

U.S. PATENT DOCUMENTS 7,204,867 B2   4/2007   Nielsen et al.
7,424,808 B2   9/2008   Mak
(Continued)

FOREIGN PATENT DOCUMENTS

WO   2022226230 A1   10/2022

OTHER PUBLICATIONS

PCT Search Report and Written Opinion dated Jul. 21, 2022, PCT Application No. PCT/US2022/025825 filed Apr. 21, 2022.
(Continued)

*Primary Examiner* — Michael L Hobbs
(74) *Attorney, Agent, or Firm* — Andrew M. Metrailer; Thaddeus J. Faleski; Conley Rose, P.C.

(57) ABSTRACT

Ammonia, methanol, Fischer Tropsch products, and derivatives thereof are made by using hydrogen and oxygen supplied from an electrolyzer that is at least partially powered by renewable power, resulting in green process and systems that produce green products disclosed herein. A process using biomass and renewable energy includes producing an unshifted syngas from biomass and oxygen in a gasification unit, introducing water into an electrolyzer to produce an oxygen product and a hydrogen product, and introducing the oxygen product to the gasification unit. The electrolyzer is powered by renewable energy, and the oxygen product supplies at least a portion of the oxygen to the gasification unit.

20 Claims, 4 Drawing Sheets

(51) Int. Cl.
- *B01D 53/18* (2006.01)
- *B01J 6/00* (2006.01)
- *C01B 32/50* (2017.01)
- *C01C 1/04* (2006.01)
- *C07C 1/04* (2006.01)
- *C07C 29/151* (2006.01)
- *C07C 273/02* (2006.01)
- *C07C 273/04* (2006.01)
- *C10G 2/00* (2006.01)
- *C25B 1/04* (2021.01)
- *C25B 9/17* (2021.01)
- *C25B 15/08* (2006.01)

(52) U.S. Cl.
CPC .............. *B01D 53/18* (2013.01); *B01J 6/008* (2013.01); *C01B 32/50* (2017.08); *C01C 1/04* (2013.01); *C07C 1/0485* (2013.01); *C07C 29/1518* (2013.01); *C07C 273/025* (2013.01); *C07C 273/04* (2013.01); *C10G 2/30* (2013.01); *C25B 1/04* (2013.01); *C25B 9/17* (2021.01); *C25B 15/081* (2021.01); *C25B 15/083* (2021.01); *C01B 2203/0266* (2013.01); *C01B 2203/0283* (2013.01); *C01B 2203/0415* (2013.01); *C01B 2203/042* (2013.01); *C01B 2203/061* (2013.01); *C01B 2203/062* (2013.01); *C01B 2203/068* (2013.01); *C01B 2203/0805* (2013.01)

(58) Field of Classification Search
CPC ........ C01B 2203/042; C01B 2203/061; C01B 2203/062; C01B 2203/068; C01B 2203/0805; C01B 2203/0485; C01C 1/04; C01C 1/0488; C07C 1/0485; C07C 29/1518; C07C 273/025; C07C 273/04; C07C 31/04; C10G 2/30; C25B 1/04; C25B 9/17; C25B 15/081; C25B 15/083; B01D 53/1418; B01D 53/1475; B01D 53/18; B01J 6/008; C10J 2300/1662; C10J 2300/1668; C10J 2300/169; C10J 2300/0485; C10J 2300/0916; C10J 2300/0956; C10J 2300/0959; C10J 2300/1618; C10J 2300/1659; C10J 2300/1665; C10J 2300/1684; C10J 2300/1807; C10J 3/00; C10K 1/005; C10K 3/04

See application file for complete search history.

(56) References Cited

U.S. PATENT DOCUMENTS

| | | |
|---|---|---|
| 8,377,403 B2 | 2/2013 | Mak |
| 8,480,982 B2 | 7/2013 | Mak et al. |
| 8,845,788 B2 | 9/2014 | Mak |
| 8,876,951 B2 | 11/2014 | Mak |
| 9,114,351 B2 | 8/2015 | Mak |
| 9,163,180 B2 | 10/2015 | Marion et al. |
| 9,248,398 B2 | 2/2016 | Mak |
| 9,295,940 B2 | 2/2016 | Mak |
| 10,000,713 B2 | 6/2018 | Mak |
| 10,150,926 B2 | 12/2018 | Mak |
| 10,882,800 B2 | 1/2021 | Kramer et al. |
| 2010/0175320 A1 | 7/2010 | Schuetzle et al. |
| 2018/0171250 A1* | 6/2018 | Chapman ................ C10L 3/08 |
| 2020/0017422 A1* | 1/2020 | Kramer ................ C10L 3/08 |

OTHER PUBLICATIONS

International Preliminary Report on Patentability dated Nov. 2, 2023, PCT Application No. PCT/US2022/025825 filed Apr. 21, 2022.

* cited by examiner

PRODUCTION OF AMMONIA, METHANOL, AND SYNTHESIS PRODUCTS FROM ONE OR MORE GASIFICATION PRODUCTS

CROSS-REFERENCE TO RELATED APPLICATIONS

This application claims the benefit of U.S. Provisional Application No. 63/179,023, filed on Apr. 23, 2021, and entitled "PRODUCTION OF AMMONIA, METHANOL, AND SYNTHESIS PRODUCTS FROM ONE OR MORE GASIFICATION PRODUCTS", which is incorporated herein by reference in its entirety for all purposes.

TECHNICAL FIELD

The present disclosure relates to the production of one or more of ammonia, methanol, Fischer Tropsch products, and derivatives thereof.

BACKGROUND

Biomass and municipal solid waste (MSW) are growing problems because disposal thereof, whether by burning, incineration, or placing in landfills, results in significant sources of carbon dioxide and methane emissions. As the global population increases, so does the rate of generation of biomass and MSW and the burden for disposing of these waste materials. Moreover, there is increasing need to find cleaner energy sources for producing chemicals and fuels while reducing carbon dioxide emissions during production of the chemicals and fuels

BRIEF DESCRIPTION OF THE DRAWINGS

The following figures illustrate embodiments of the subject matter disclosed herein. The claimed subject matter may be understood by reference to the following description taken in conjunction with the accompanying figures, in which:

DESCRIPTION

Figure 1:
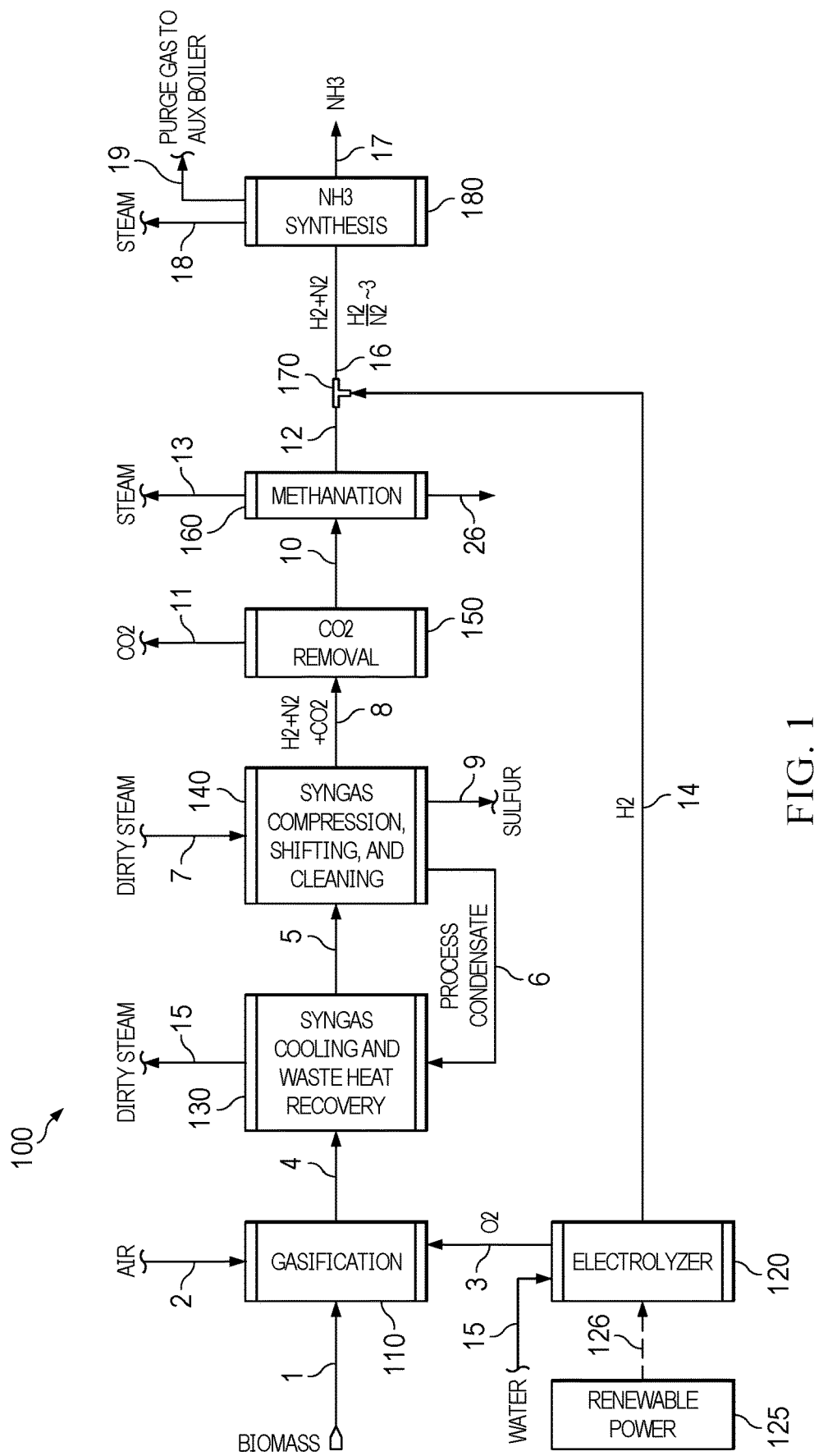
FIG. 1 illustrates a process and system for producing green ammonia from biomass and water.

It should be understood at the outset that although an illustrative implementation of one or more embodiments are provided below, the disclosed process and system may be implemented using any number of techniques, whether currently known or in existence. The disclosure should in no way be limited to the illustrative implementations, drawings, and techniques illustrated hereinbelow, including the exemplary designs and implementations illustrated and described herein, but may be modified within the scope of the appended claims along with their full scope of equivalents. Thus, while multiple embodiments are disclosed, still other embodiments will become apparent to those skilled in the art from the following detailed description. As will be apparent, some embodiments, as disclosed herein, are capable of modifications in various aspects without departing from the spirit and scope of the claims as presented herein. Accordingly, the detailed description hereinbelow is to be regarded as illustrative in nature and not restrictive.

The recitation of ranges of values herein is merely intended to serve as a shorthand method of referring individually to each separate value falling within the range. Unless otherwise indicated herein, each individual value is incorporated into the specification as if it were individually recited herein. All processes described herein can be performed in any suitable order unless otherwise indicated herein or otherwise clearly contradicted by context. The use of any and all examples, or exemplary language (e.g., "such as") provided with respect to certain embodiments herein is intended merely to better illuminate the disclosure and does not pose a limitation on the scope of the disclosed subject matter otherwise claimed. No language in the specification should be construed as indicating any non-claimed element essential to the practice of the disclosed subject matter.

Groupings of alternative elements or embodiments disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified.

The following discussion provides many exemplary embodiments of the disclosed subject matter. Although each embodiment may represent a single combination of disclosed elements, the disclosed subject matter is considered to include all possible combinations of the disclosed elements. Thus, if one embodiment comprises elements A, B, and C, and a second embodiment comprises elements B and D, then the disclosed subject matter is also considered to include other remaining combinations of A, B, C, or D, even if not explicitly disclosed.

While the following terms are believed to be well understood by one of ordinary skill in the art, the following definitions are set forth to facilitate explanation of the presently disclosed subject matter. Unless defined otherwise, all technical and scientific terms used herein have the same meaning as commonly understood to one of ordinary skill in the art to which the presently disclosed subject matter belongs.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

As used herein, the terms "comprise," "comprises," "comprising," or any other variations thereof, are intended to cover a non-exclusive inclusion, such that a process or method that comprises a list of steps does not include only those steps but may include other steps not expressly listed or inherent to such process or method. Similarly, one or more devices or sub-systems or elements or structures preceded by "comprises [ . . . ] a" does not, without more constraints, preclude the existence of other devices or other sub-systems or other elements or other structures or additional devices or additional sub-systems or additional elements or additional structures.

Reference throughout this specification to "one embodiment," "an embodiment," or similar language means that a particular feature, structure, or characteristic described in connection with the embodiment is included in at least one embodiment of the present disclosure. Thus, appearances of the phrase "in one embodiment," "in an embodiment," and similar language throughout this detailed description may, but do not necessarily, all refer to the same embodiment.

As used herein, the term "splitter" refers to a joint of conduit or pipe that functions to split a stream, line, conduit, or pipe into two streams, lines, conduits, or pipes. For example, a "splitter" can be embodied as a joint having three flow openings: an inlet opening for receiving the flow of fluid, and two outlet openings for flowing fluid out of the splitter, where the received fluid flow is split into two separate flow portions within the splitter. To accommodate a flow rate through one outlet opening that is different than the flow rate through the other outlet opening, the diameter of the two outlet openings can be appropriately sized to facilitate the desired flow or "split percentage" disclosed herein; or in alternative aspects, within the scope of "splitter" as used herein is equipment, such as valving and instrumentation, that can control the flow of fluid through each outlet opening to achieve a "split percentage" that is disclosed herein.

As used herein, the term "combiner" refers to a joint of conduit or pipe that functions to combine the flow of two streams, lines, conduits, or pipe into one stream, line, conduit, or pipes. For example, a "combiner" can be embodied as a joint having three flow openings: two inlet openings for receiving the flow of fluid, and one outlet opening for flowing fluid out of the combiner, where the received fluid flow is combined into a single stream, line, conduit, or pipe.

Disclosed herein is a process for using biomass and/or a municipal solid water gasification system in combination with water electrolysis to produce various products such as green ammonia, green methanol, green derivatives of ammonia and methanol, and various green Fischer Tropsch products such as diesel, jet fuel, lubrication oils and greases, and waxes. The products may be considered green by using renewable power as the electricity source in the electrolysis unit to produce oxygen and hydrogen. The resulting oxygen and hydrogen can then be used in separate portions of the system to generate the products. For example, the oxygen can be used in the gasification unit to avoid the need for an air separation unit to otherwise generate oxygen.

Such a system and methods allow for the use of biomass to produce value added products that are green and avoid placing the biomass and waste into a landfill while also avoiding associated carbon dioxide and methane generation in various landfill applications. The ability to produce products such as ammonia and/or urea may also allow the use of the products in fuel cells.

Each process and system described herein produces a green product because the feed to the gasification unit 110 may be biomass and/or municipal waste 1 and the electrolysis unit 120 may be powered at least partially, and optionally wholly, by renewable power 126, such as solar, wind, or geothermal. Moreover, each process and system can remove carbon dioxide to produce a CO2 product 11 that can be sequestered, stored, used (e.g., in secondary hydrocarbon recovery or as described herein), or a combination thereof.

The gasification unit 110 can be embodied as one or more vessels in plasma configuration, a fixed-bed configuration, or a fluidized-bed configuration that are configured to gasify biomass in the presence of oxygen (and optionally nitrogen via air supply) to produce syngas. Various configurations for gasification unit 110 are known in the art with the aid of this disclosure.

The electrolysis unit 120 can be embodied as one or more vessels having a cathode and anode therein that are configured to receive water and use electricity to decompose water molecules into hydrogen and oxygen gas. Configurations for electrolysis 120 are known in the art with the aid of this disclosure.

Each process and system described herein includes a gasification unit 110 and an electrolysis unit 120 coupled to the gasification unit 110. In this disclosure, the gasification unit 110 may be coupled to the electrolysis unit 120 to receive an oxygen product 3 from the electrolysis unit 120 so that oxygen product 3 be used in the gasification process. The electrolysis unit 120 can be coupled to renewable energy source 125 and to the gasification unit 110 so that the oxygen product 3, made by electrolysis of water in the electrolysis unit 120 with electricity supply from the renewable energy source 125, can be used in the gasification process. Moreover, the hydrogen product 14 produced by the electrolysis unit 120 can be combined with a treated syngas stream that may be downstream of the gasification unit 110 (e.g., a treated gasification product 12 in FIGS. 1 and 2; a treated gasification product 10A in FIGS. 3 and 4) to enrich the syngas with hydrogen and to form a synthesis feed stream (stream 16 in FIGS. 1 and 2; stream 101 in FIGS. 3 and 4) that may be suitable as a feed to a synthesis unit configured to produce ammonia, methanol, or Fischer Tropsch products. A portion of the hydrogen product 14 can also be fed to an upgrading unit for upgrading the Fischer Tropsch products (described in more detail for FIG. 4).

The process and system 100 in FIG. 1 feeds a biomass 1, air 2, and oxygen product 3 to the gasification unit 110 to produce an unshifted syngas 4. The unshifted syngas 4 can include hydrogen, carbon monoxide, and optionally: carbon dioxide, methane (e.g., unreacted methane, unreformed methane), sulfur-containing compounds in case of passivated reformer catalyst (e.g., hydrogen sulfide, carbon sulfide, carbonyl sulfide, carbon disulfide, organic sulfur compounds, etc.), chlorides, steam, or a combination thereof.

In some embodiments, the unshifted syngas 4 can be characterized by a molar ratio of hydrogen to carbon monoxide of from about 1.7:1 to about 2.5:1, alternatively from about 1.8:1 to about 2.3:1, or alternatively from about 1.9:1 to about 2.1:1, for example if a reformer including a sulfur passivated nickel-based catalyst may be used, such as a new reformer. In an embodiment, the unshifted syngas 4 can have a molar ratio of hydrogen to carbon monoxide of about 2:1. In other embodiments, the unshifted syngas 4 can be characterized by a molar ratio of hydrogen to carbon monoxide of from about 3:1 to about 4:1, for example if a reformer comprising a sulfur sensitive nickel-based catalyst may be used, such as an existing reformer.

In some embodiments, the unshifted syngas 4 can include carbon dioxide in an amount of less than about 20 mole % (mol %), alternatively less than about 10 mol %, or alternatively less than about 5 mol %, for example if a reformer including a sulfur passivated nickel-based catalyst may be used, such as a new reformer. In other embodiments, the unshifted syngas 4 can include carbon dioxide in an amount of less than about 50 mol %, for example if a reformer including a sulfur sensitive nickel-based catalyst may be used, such as an existing reformer (e.g., conventional reformer).

In an embodiment, the unshifted syngas 4 can include methane (e.g., unreacted methane, unreformed methane) in an amount of less than about 5 mol %, alternatively less than about 2.5 mol %, alternatively less than about 2 mol %, or alternatively less than about 1 mol %.

In other embodiments, the unshifted syngas 4 can include sulfur-containing compounds in an amount of less than about 1 parts per million volume (ppmv). As will be appreciated by one of skill in the art, and with the help of this disclosure, a portion of syngas contaminants (e.g., sulfur-containing compounds, chlorides, etc.) can be in a gas state in the syngas 4, and a portion of the contaminants can be dissolved in the water present in the syngas 4.

In some embodiments, the unshifted syngas 4 can have a pressure of from about 5 pounds per square inch gauge (psig) to about 50 psig, for example if a reformer including a sulfur passivated nickel-based catalyst may be used, such as a new reformer. In other embodiments, the unshifted syngas 4 can have a pressure of from about 300 psig to about 500 psig, for example if a reformer including a sulfur sensitive nickel-based catalyst may be used, such as an existing reformer.

The process can further include introducing the unshifted syngas (e.g., via the stream 4) to a water gas shift unit 140 to produce a shifted syngas (e.g., in the stream 5). In embodiments, the shifted syngas 5 comprises hydrogen, carbon monoxide, and carbon dioxide. The molar ratio of hydrogen to carbon monoxide in the unshifted syngas 4 can be increased (e.g., adjusted) by introducing the unshifted syngas 4 to a water gas shift unit 140 comprising a sour shift catalyst to convert carbon monoxide and water into additional hydrogen and carbon dioxide according to the general reaction $CO+H_2O \leftrightarrow H_2+CO_2$, also known as the water-gas shift (WGS) reaction. The WGS reaction can be conducted in the presence of a variety of sour shift catalysts at a WGS reaction temperature of from about 204.4° C. to about 482.2° C., alternatively from about 232.2° C. to about 454.5° C., or alternatively from about 260° C. to about 426.7° C. The WGS reaction does not change the total number of moles (e.g., two moles of products are produced from two moles of reactants), and as such an effect of pressure on the WGS reaction may be minimal. The equilibrium of the WGS reaction can be shifted towards hydrogen production in the presence of high moisture content. Generally, excess moisture can be present in the unshifted syngas 4 that may be recovered from the reformer, and such moisture is usually sufficient to drive the WGS reaction to achieve a desired molar ratio of hydrogen to carbon monoxide. In an embodiment, steam can be further introduced to the water gas shift unit 140 to increase the moisture content.

In some embodiments, the unshifted syngas 4 can be heated to a temperature that may be greater than a syngas moisture saturation temperature by from about 11.1° C. to about 41.7° C., alternatively from about 13.8° C. to about 33.3° C., or alternatively from about 16.6° C. to about 27.8° C., prior to introducing the unshifted syngas 4 to the water gas shift unit 140. As will be appreciated by one of skill in the art with the help of this disclosure, if the temperature of the unshifted syngas 4 may be too low, the water could condense inside the water gas shift unit 140 and such water condensation could damage a sour shift catalyst. The syngas moisture saturation temperature can be from about 176.6° C. to about 260° C., depending on the unshifted syngas 4 composition and process conditions for producing the unshifted syngas 4.

In an embodiment, the water gas shift unit 140 can comprise any suitable reactor, such as for example a fixed bed reactor, an adiabatic reactor, a radial reactor, and the like, or combinations thereof. In an embodiment, a water gas shift reactor can comprise a catalyst bed comprising a sour shift catalyst in sulfur that may be present in the feed syngas. In an embodiment, the water gas shift unit 140 can be a multi-stage unit, for example the water gas shift unit 140 can comprise multiple reactors and/or multiple fixed beds.

The WGS reaction can be catalyzed by both metals and metal oxides. Non-limiting examples of sour shift catalysts suitable for use include cobalt, molybdenum, copper, iron, a cobalt-molybdenum catalyst, a chromium promoted iron-based catalyst, a copper promoted iron-based catalyst, a copper-zinc-aluminum catalyst, copper oxide (CuO), iron oxide ($Fe_2O_3$), oxides thereof, and the like, or combinations thereof. Sweet shift catalysts are generally iron based.

In an embodiment, a molar ratio of hydrogen to carbon monoxide in the shifted syngas can be greater than a molar ratio of hydrogen to carbon monoxide in the unshifted syngas. In an embodiment, the shifted syngas can be characterized by a molar ratio of hydrogen to carbon monoxide of equal to or greater than about 100:1, alternatively from about 5:1 to about 100:1, alternatively from about 10:1 to about 75:1, or alternatively from about 15:1 to about 40:1. As will be appreciated by one of skill in the art, and with the help of this disclosure, the molar ratio of hydrogen to carbon monoxide depends on shifting (e.g., CO conversion via the WGS reaction) conditions (e.g., type of WGS unit, type of catalyst used in the WGS unit, etc.). Further, as will be appreciated by one of skill in the art, and with the help of this disclosure, full shifting (e.g., almost all CO undergoes the WGS reaction) can lead to hydrogen to carbon monoxide molar ratios of over 10:1 due to very small CO numbers; single stage, mild shifting can lead to hydrogen to carbon monoxide molar ratios of from about 5:1 to about 10:1; a more moderate level of full shift can lead to hydrogen to carbon monoxide molar ratios of about 7:1; and the hydrogen to carbon monoxide molar ratio decreases with catalyst age.

In an embodiment, an amount of carbon dioxide in the shifted syngas can be greater than an amount of carbon dioxide in the unshifted syngas. As will be appreciated by one of skill in the art, and with the help of this disclosure, carbon dioxide may be produced in equimolar amounts with hydrogen via the WGS reaction. In aspects, the shifted syngas in the stream 5 also contains unreacted steam.

The compressing steps disclosed herein can be performed with one or more gas compressors that are locating in the unit 140. When multiple compressors are present, the compressors can be connected in series, in parallel, or in series and in parallel. The compressor(s) can be any compressor known in the art for compressing streams containing syngas.

The unshifted syngas 4 can then be cooled in a heat exchanger 130 to form a cooled syngas 5, followed by compressing, shifting, and cleaning (e.g., to remove sulfur-containing compounds) the syngas in unit 140 to form a shifted syngas 8 and a sulfur product 9. Because the gasification unit 110 may be configured to receive air 2 (containing oxygen and nitrogen), the shifted syngas 8 contains nitrogen in addition to hydrogen, carbon monoxide, and carbon dioxide. Carbon dioxide can be separated from the shifted syngas 8 in an absorption unit 150 to produce a CO2 product 11 and a CO2 depleted syngas 10 containing nitrogen, carbon monoxide, and hydrogen. The CO2 product 11 can be sequestered, stored, or used (e.g., in secondary hydrocarbon recovery). The CO2 depleted syngas 10 can be subjected to methanation in a methanation unit 160 so as to convert carbon monoxide and carbon dioxide (COx) molecules to methane and water, thereby producing steam and a methanation product stream containing methane, hydrogen, and nitrogen. The steam can be removed from the methanation unit in stream 13. In any embodiment, the methane may be passed in a treated gasification product 12 to the ammonia synthesis unit 180 where a purge stream 19 prevents accumulation of methane and inert gases such as argon. In some embodiments, the methanation unit 160 can include a separator that may be configured to separate the methane from the hydrogen and nitrogen to produce the treated gasification product 12 containing hydrogen and nitrogen and to produce a methane product 26 that can be used as fuel for plant needs.

The process and system 100 in FIG. 1 uses renewable power 126 to operate an electrolysis unit 120 that separates water 15 into hydrogen (in hydrogen product 14) and oxygen (in oxygen product 3). The electrolysis unit 120 may be coupled to a renewable energy source 125 so as to receive the renewable power 126. The oxygen can be fed to the gasification unit 110 via the oxygen product 3, and the hydrogen can flow in a hydrogen product 14 that combines with the treated gasification product 12 via a combiner 170 to form an ammonia synthesis feed stream 16.

In aspects, the mole ratio of hydrogen to nitrogen in the ammonia synthesis feed stream 16 can be between about 2:1 to about 4:1, or about 3:1. In further aspects, the mole ratio of hydrogen to nitrogen in the ammonia synthesis feed stream 16 may be controlled to be between about 2:1 to about 4:1, or about 3:1. The flow of hydrogen in the hydrogen product 14, relative to the flow of the treated gasification product 12, can be controlled such that the mole ratio of hydrogen to nitrogen in the ammonia synthesis feed stream 16 can be between about 2:1 to about 4:1, or about 3:1. In aspects, the treated gasification product 12, the hydrogen product 14, and the ammonia synthesis feed stream 16 can have sensors, control valves, and associated instrumentation configured to measure the amount of hydrogen and nitrogen in one or more of the treated gasification product 12, the hydrogen product 14, and the ammonia synthesis feed stream 16 and to control the flow of hydrogen in the hydrogen product 14 to the combiner 170 such that the process and system 100 control the mole ratio of hydrogen to nitrogen in the ammonia synthesis feed stream 16 to be between about 2:1 to about 4:1, or about 3:1.

The ammonia synthesis feed stream 16 can be fed to an ammonia synthesis unit 180 where an ammonia product 17 may be produced. The ammonia product 17 may be considered green ammonia because the feed to the gasification unit 110 may be biomass 1, air 2, and oxygen product 3 that may be made utilizing renewable power 126. The ammonia synthesis unit 180 can produce steam 18 and the purge gas 19. The steam 18 can be used as steam 7, in some aspects. In some aspects, the purge gas 19 can be used in an auxiliary boiler.

In aspects, the steam 13 that may be removed from the methanation unit 160 can be used in unit 140 for shifting the unshifted syngas 4. Moreover, the unit 140 can recover a process condensate 6 (aqueous condensate) that can be used as coolant in the heat exchanger 130, the heating of the condensate in the heat exchanger 130 thereby producing steam 15.

The heat exchanger 130 can be configured as a cross-exchanger, where one side of the heat exchanger 130 may be the syngas side, and the other side of the heat exchanger 130 contains the coolant that cools the syngas 4 and may be the coolant side. The syngas side of the heat exchanger 130 may be configured to receive the syngas 4 and cool the syngas. The cooled syngas 5 exits the syngas side of the heat exchanger 130 in stream 5. The coolant side of the heat exchanger 130 receives the aqueous condensate 6 that may be heated by contact with the syngas side inside the heat exchanger 130. Heating the coolant produces steam which flows from the heat exchanger 130 via stream 15.

Figure 2:
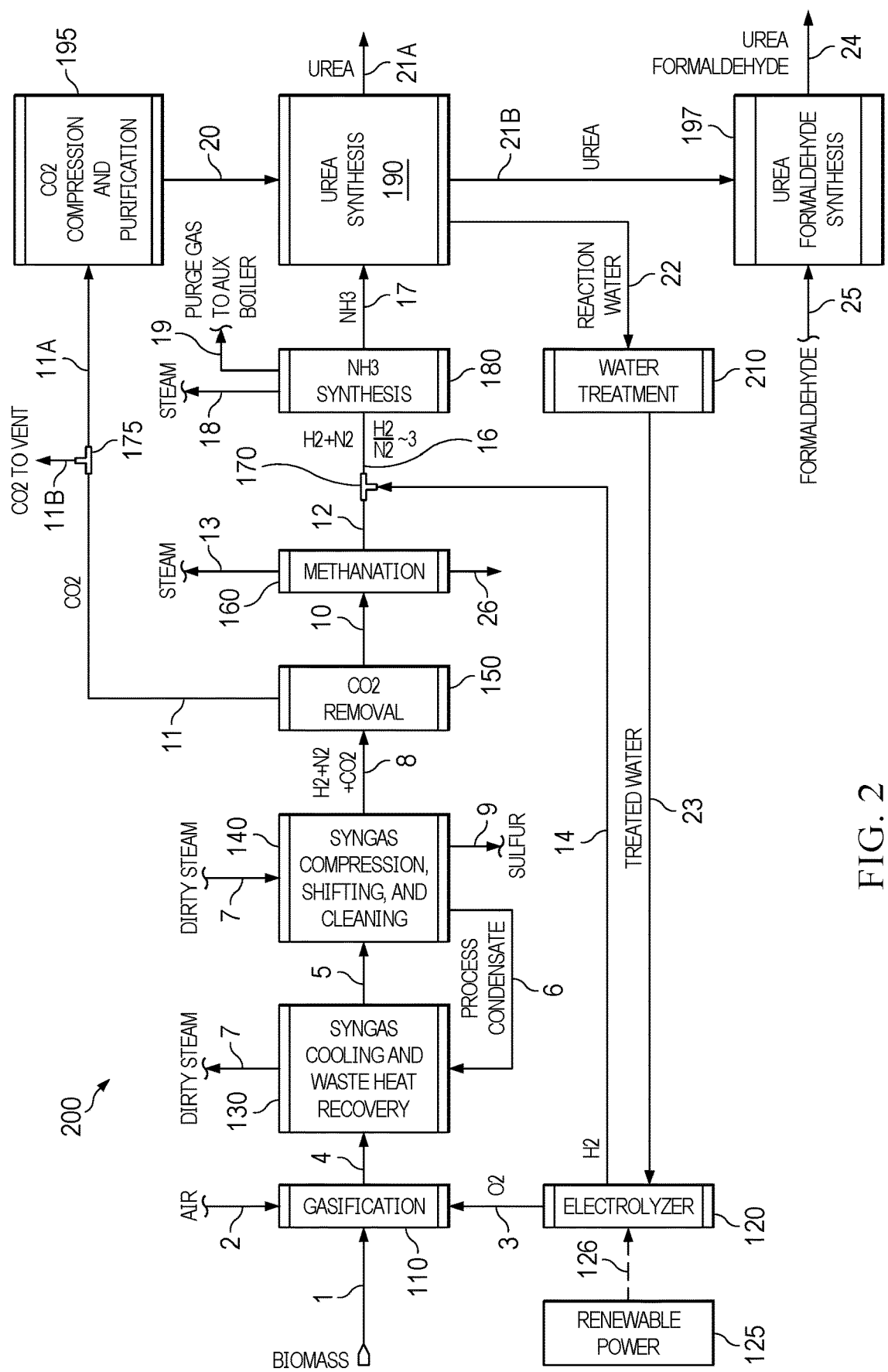
FIG. 2 illustrates a process and system for producing green urea and derivatives from biomass and water.

The process and system 200 in FIG. 2 feeds a biomass 1, air 2, and oxygen product 3 to the gasification unit 110 to produce an unshifted syngas 4. The unshifted syngas 4 can then be cooled in a heat exchanger 130 to form a cooled syngas 5, followed by compressing, shifting, and cleaning (e.g., to remove sulfur-containing compounds) the syngas in unit 140 to form a shifted syngas 8 and a sulfur product 9.

Because the gasification unit 110 may be configured to receive air 2 (containing oxygen and nitrogen), the shifted syngas 8 contains nitrogen in addition to hydrogen, carbon monoxide, and carbon dioxide. Carbon dioxide can be separated from the shifted syngas 8 in an absorption unit 150 to produce a CO2 product 11 and a CO2 depleted syngas 10 containing nitrogen, carbon monoxide, and hydrogen.

Figure 3:
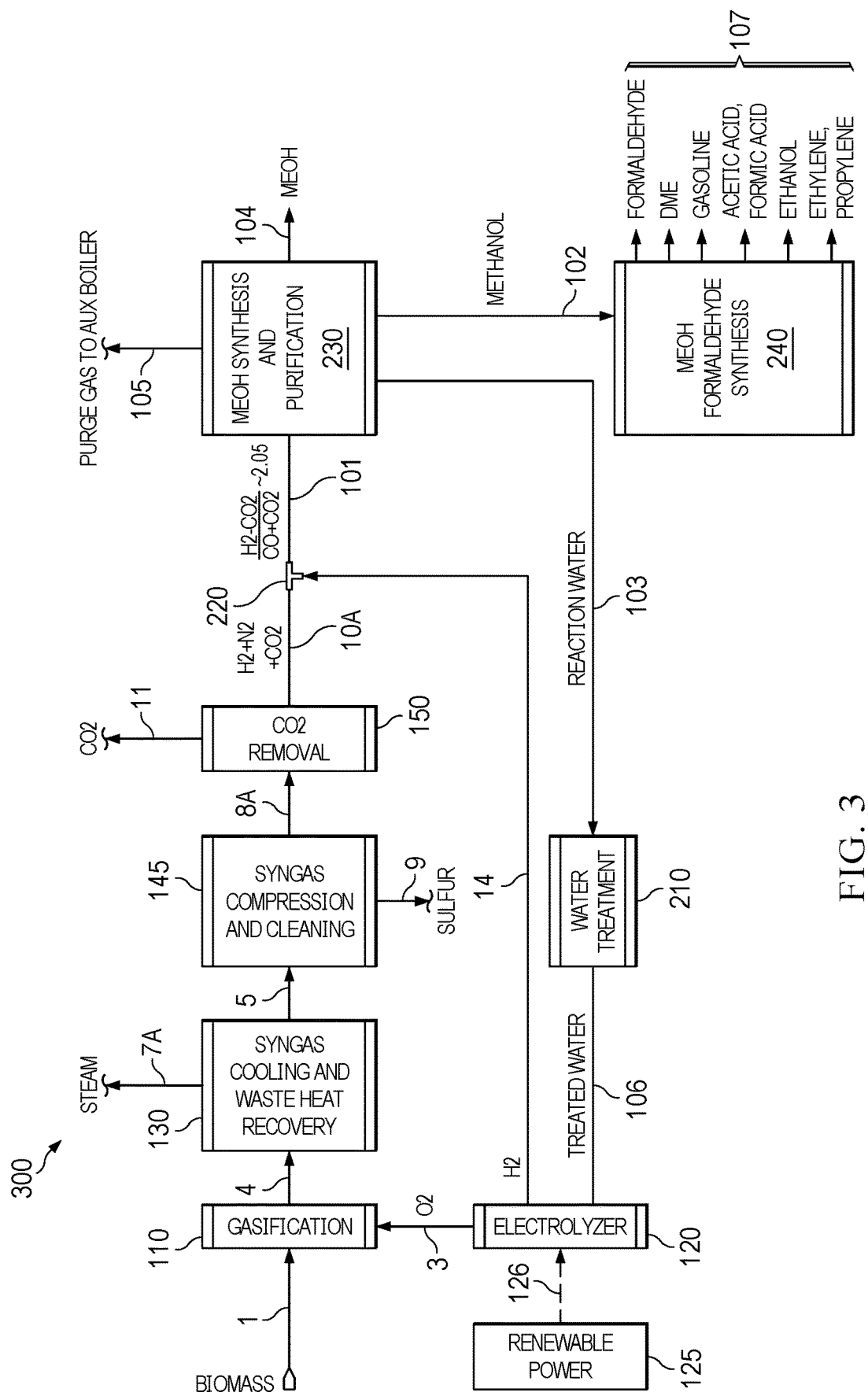
FIG. 3 illustrates a process and system for producing green methanol and derivatives from biomass and water.
Figure 4:
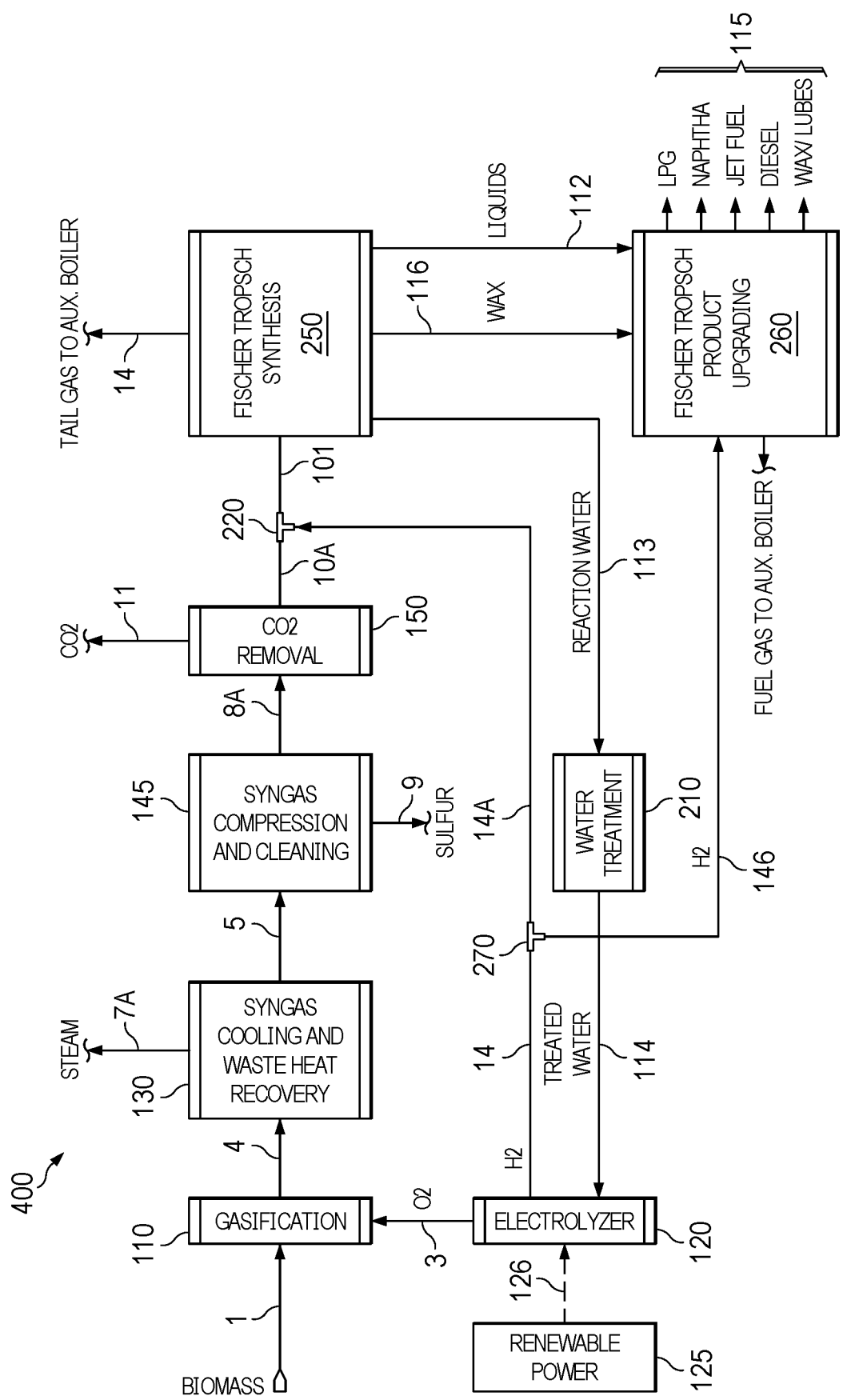
FIG. 4 illustrates a process and system for producing green hydrocarbon products from biomass and water.

The absorption unit 150 as illustrated in the figures may be generally configured to receive the cooled shifted syngas in stream 8 (FIGS. 1-2) or the cooled syngas 8A (FIGS. 3-4), to remove CO2 from the respective syngas to produce the CO2 product in stream 11 and the CO2 depleted syngas in stream 10 (FIGS. 1-2) or the treated gasification product 10A (FIGS. 3-4).

Removing CO2 from the shifted syngas can include absorbing CO2 with a lean solvent to produce the CO2 depleted syngas 10 or treated gasification product 10A and a CO2 enriched solvent, and flashing the CO2 enriched solvent to produce the CO2 product and the lean solvent. Flashing does not require a stripper, so there may be no steam needed to remove CO2 when using certain solvents. In some aspects, the solvent may be a physical solvent. Moreover, using a physical solvent allows for the equipment in the absorption unit 150 to be made of carbon steel (not made of any stainless steel). In some aspects, the solvent may comprise both a physical solvent and a chemical solvent.

Alternatively, removing CO2 can include absorbing CO2 with a chemical solvent such as a lean amine solvent to produce the CO2 depleted syngas 10 or treated gasification product 10A and a CO2 enriched amine solvent, and stripping the CO2 enriched amine solvent to produce the CO2 product and the lean amine solvent to produce the CO2 product and the lean amine solvent or other CO2 removal technologies.

In an embodiment, the absorption unit 150 can include an absorber and regenerator, where at least a portion of the carbon dioxide can be removed (e.g., recovered, separated, etc.) from at least a portion of the cooled shifted syngas by a physical solvent and/or a chemical solvent in the absorber. In aspects, the absorption unit 150 can include the absorber having a lean physical solvent configured to absorb carbon dioxide from the shifted syngas to produce a CO2 enriched solvent and the CO2 depleted syngas in the stream 10. The absorption unit 150 can also include a flash tank coupled to the absorber, wherein the flash tank may be configured to receive the CO2 enriched solvent from the absorber and to flash carbon dioxide from the CO2 enriched solvent to produce the lean physical solvent and the CO2 product in the stream 11. Alternatively, the absorption unit 150 can include an absorber having a lean chemical solvent configured to absorb carbon dioxide from the shifted syngas to produce a CO2 enriched solvent and the CO2 depleted syngas in the stream 10, and a stripper coupled to the absorber, wherein the stripper may be configured to receive the CO2 enriched solvent from the absorber and to strip carbon dioxide from the CO2 enriched solvent to produce the lean chemical solvent and the CO2 product in the stream 5.

In aspects where the absorption solvent may be a chemical solvent, the regenerator can be embodied as a stripper configured to use a stripping gas to remove the carbon dioxide from the chemical solvent. The stripper can include a reboiler that provides heat to the stripper for removing carbon dioxide from the chemical solvent to produce the lean chemical solvent. In aspects, the stripper can comprise any suitable stripping column, wherein a gas phase (e.g., the carbon dioxide) may be removed from the liquid phase (e.g., the CO2 enriched solvent). Generally, the stripper can be similar in configuration to the absorber, while operating at different parameters (e.g., pressure, temperature, etc.). A pressure in the stripper can be lower than a pressure in the absorber and a temperature in the stripper can be higher than a temperature in the absorber, to enable the CO2 enriched solvent to release carbon dioxide. Generally, the stripper can be one or more vertical and cylindrical columns or towers. In an embodiment, the CO2 enriched solvent can be introduced as a downflow at the top of the stripper, and a portion of the lean solvent can be re-introduced at the bottom (e.g., bubbled) of the stripper as vapor (e.g., using a reboiler). In such embodiment, carbon dioxide can be recovered at the top of the stripper, and the lean solvent can be recovered at the bottom of the stripper. Generally, a reboiler for the stripper can be heated with steam (e.g., low pressure steam at a pressure of from about 400 kPa to about 1,500 kPa), wherein the steam can be recovered from the reboiler as an aqueous condensate, and wherein the recovered aqueous condensate can be further converted into the steam used for heating the reboiler. In some embodiments, the stripper can comprise a packed bed column, a tray column, a spray column, a falling film column, a bubble column, a sparged tank column, and the like, or combinations thereof. In an embodiment, the stripper can operate at a pressure of from about 5 psig to about 50 psig, alternatively from about 10 psig to about 45 psig, alternatively from about 20 psig to about 40 psig, alternatively from about 25 psig to about 35 psig, or alternatively from about 25 psig to about 30 psig.

Examples of chemical solvent useful in the absorption unit 150 include primary amines, secondary amines, tertiary amines, sterically hindered amines, methylethylamine (MEA), methyl diethanolamine (MDEA), diglycolamine (DGA), 2-amino-2-methyl-1-propanol (AMP), or a combination thereof.

In aspects where the absorption solvent may be a physical solvent, the regenerator can be embodied as a flash tank or flash column configured to remove the carbon dioxide from the CO2 rich physical solvent by pressure reduction, i.e., flashing (e.g., via pressure reduction) the carbon dioxide out of the physical solvent. In aspects, the flash tank can comprise any suitable vessel, wherein a gas phase (e.g., the carbon dioxide) may be flashed by differential pressure from the liquid phase (e.g., the CO2 enriched solvent). Generally, the flash tank can be any vessel configured to subject the CO2 enriched solvent to a drop in pressure such that the carbon dioxide may be liberated from the liquid solvent to form the lean physical solvent. A pressure in the flash tank may be generally lower than a pressure in the absorber to enable the carbon dioxide to flash from CO2 enriched solvent to produce the lean physical solvent and the CO2 product in stream 11. In an embodiment, the flash tank can operate at a pressure in a range of from a vacuum pressure to about 200 psig (1.38 MPag). In some embodiments, the flash tank may be one or more vessels (e.g., more than one flash tank) connected in series such that the reduction in pressure may be accomplished in stages.

Examples of physical solvents useful in the absorption unit 150 include methanol, propylene carbonate, N-methylpyrrolidone, a glycol ether, ethers of polyglycols (e.g., dimethoxytetraethylene glycol or N-substituted morpholine), or a combination thereof. In some embodiments, the absorption solvent can comprise a propylene carbonate having favorable treating properties such as high solubility for carbon dioxide, low heat solution of carbon dioxide, low solvent vapor pressure, low solvent freezing temperature, non-hazardous, non-reactive to natural gas components, non-degradable or non-foamable, water absorbent, and low solubility for light hydrocarbons and low viscosity. Regarding water absorbability, such a property allows the use of cheaper materials, such as carbon steel, in e.g., the absorption unit 150. Some embodiments may use a process sold under the trade designation Fluor Solvent$^{SM}$ system comprising or consisting of a propylene carbonate solvent available from Fluor Corporation of Irving, Texas.

The chemical solvent and/or physical solvent can absorb the carbon dioxide while the remaining components of the received syngas pass through the absorber to form the CO2 depleted syngas in stream 10 or the treated gasification product in stream 10A. The carbon dioxide in the CO2 enriched solvent leaves the absorber and may be fed to a regenerator, where the carbon dioxide may be separated from the solvent (the solvent may be regenerated) to produce a lean solvent (e.g., a lean physical solvent or a lean chemical solvent) and a CO2 product. The lean solvent can be recycled to the absorber, and the CO2 product may be recovered in stream 11. In an embodiment, the absorber can comprise any suitable absorber column, wherein a gas phase (e.g., the cooled shifted syngas) interacts with a liquid phase (e.g., absorption solvent) via co-current flow, counter-current flow, or cross-flow. Generally, absorption columns can be vertical and cylindrical columns or towers. In an embodiment, the absorber can comprise a countercurrent absorber column, wherein the shifted syngas can be introduced to the column countercurrent (e.g., opposing flow directions) with respect to the flow of absorption solvent. In an embodiment, the absorption solvent can be introduced as a downflow at the top of the absorber, and the received syngas can be introduced (e.g., bubbled) at the bottom of the absorber. In such embodiment, the CO2 depleted syngas or treated gasification product can be recovered at the top of the absorber, and the CO2 enriched solvent can be recovered at the bottom of the absorber. The absorber can have one or more trays and/or packing as a contacting device. However, any other suitable contacting devices can be employed, such as for example static or dynamic mixers, spargers, impellers, etc. In some embodiments, the absorption unit 150 can comprise a packed bed column, a tray column, a spray column, a falling film column, a bubble column, a sparged tank column, and the like, or combinations thereof. In an embodiment, the absorber can operate at a pressure of from about 375 psig to about 575 psig, alternatively from about 400 psig to about 550 psig, or alternatively from about 450 psig to about 500 psig.

In aspects, the CO2 depleted syngas in stream 10 or the treated gasification product in stream 10A can comprise substantially all of the hydrogen present in the syngas in stream 8 or 8A. In an embodiment, the CO2 depleted syngas 10 or the treated gasification product 10A can contain equal to or greater than about 50 mol %, alternatively equal to or greater than about 60 mol %, alternatively equal to or greater than about 70 mol %, alternatively equal to or greater than about 80 mol %, alternatively equal to or greater than about 90 mol %, alternatively equal to or greater than about 95 mol %, or alternatively equal to or greater than about 99 mol % of the hydrogen of the syngas 8 or 8A.

In aspects, the CO2 enriched solvent can comprise carbon dioxide in an amount of equal to or greater than about 30 mol %, alternatively equal to or greater than about 40 mol %, or alternatively equal to or greater than about 50 mol % of the carbon dioxide of the cooled syngas.

In an embodiment, the process can include sequestering the carbon dioxide product in the CO2 product stream 11. In an embodiment, the carbon dioxide product in the stream 11 can comprise substantially all of the carbon dioxide of the shifted syngas in the stream 8. In some embodiments, the carbon dioxide product can include equal to or greater than about 99 mol %, alternatively equal to or greater than about 99.5 mol %, alternatively equal to or greater than about 99.9 mol %, or alternatively equal to or greater than about 99.99 mol % of the carbon dioxide of the cooled shifted syngas in the stream 5. Alternatively, the process can include sending the carbon dioxide product in the CO2 product stream 11 to storage or a pipeline for transport, for example, for use in enhanced oil recovery.

In an embodiment, the PSA unit 150 comprises an adsorbent material. Non-limiting examples of adsorbent materials suitable for use in the present disclosure include molecular sieves, zeolites, such as 5A zeolite and 13X zeolite, and the like, or combinations thereof. Pressure swing adsorption (PSA) may be generally based on physical binding of gas molecules (e.g., hydrogen, methane, carbon dioxide, etc.) to an adsorbent material (e.g., a solid). Binding strength between the gas molecules and the adsorbent material depends on the gas components, type of adsorbent material, partial pressures of the gas components and operating temperature. Purifying a gas by the PSA separation may be based on differences in binding strength of the gas components to the adsorbent material. Highly volatile components with low polarity, such as hydrogen, are practically non-adsorbable, as opposed to molecules like methane and carbon dioxide. The PSA generally has an adsorption step, and a desorption step. During the adsorption step, high purity hydrogen can be recovered from the PSA unit 150, as hydrogen will not be adsorbed. Methane and carbon dioxide will be adsorbed by the adsorbent material, and can be recovered during the desorption step.

Although not wanting to be bound by theory, the PSA works at basically constant temperature and uses the effect of alternating pressure and partial pressure to perform the adsorption step and the desorption step. Because heating or cooling may be not required, short cycles within the range of minutes can be achieved. A cycle can be defined as the time between the start of two consecutive adsorption steps. The adsorption may be carried out at high pressure, until an equilibrium loading may be reached, wherein no further adsorption capacity is available and the adsorbent material is generally regenerated. The desorption step can be done by lowering the pressure to slightly above atmospheric pressure resulting in a respective decrease in equilibrium loading. As a result, the gases (e.g., methane, carbon dioxide) that were adsorbed by the adsorbent material are desorbed and the adsorbent material may be regenerated. Once the desorption step may be completed, the pressure may be increased back to adsorption pressure level and another adsorption step begins. Generally, the PSA also involves a purge step between the desorption step and the adsorption step, to ensure that the adsorber material may be ready to undergo the next adsorption step.

In an embodiment, the CO2 depleted syngas can be introduced to the PSA unit at the bottom, and can travel upwards through the adsorbent material, wherein hydrogen can be recovered at a top of the PSA unit during the adsorption step. In such embodiment, the PSA off-gas including methane and carbon dioxide can be recovered at the bottom of the PSA unit during the desorption step.

In an embodiment, the PSA unit 150 comprises from about 2 to about 10 PSA units, alternatively from about 3 to about 8 PSA units, alternatively from about 3 to about 6 PSA units operating in parallel, to provide a continuous supply of hydrogen, and to provide for a continuous uptake of CO2 depleted syngas. Once an adsorption step may be completed in the PSA unit 150, and such unit starts a desorption step, another PSA unit can take over the adsorption step to ensure a continuous process. As will be appreciated by one of skill in the art, and with the help of this disclosure, more than the one PSA unit can undergo the adsorption step at the same time, and similarly, more than the one PSA unit can undergo the desorption step at the same time. As long as there may be always a PSA unit undergoing an adsorption step and/or ready to undergo an adsorption step, hydrogen production can be continuous.

The CO2 product 11 can be split via a splitter 175 into a first portion 11a and a second portion 11b. The first portion 11a can be used for urea synthesis (described in more detail below), and the second portion 11b can be sequestered, stored, or used (e.g., in secondary hydrocarbon recovery). The CO2 depleted syngas 10 can be subjected to methanation in a methanation unit 160 so as to convert COx molecules to methane and water, thereby producing steam 18 and a methanation product stream 26 containing methane, hydrogen, and nitrogen. The steam can be removed from the methanation unit in stream 13. The methanation unit 160 can include a separator that may be configured to separate the methane from the hydrogen and nitrogen to produce a treated gasification product 12 containing hydrogen and nitrogen and to produce a methane product stream 26 that can be used as fuel for plant needs. In any embodiment, methane and one or more inert gases may be purged at the ammonia synthesis unit 180, as discussed above.

The process and system 200 in FIG. 2 uses renewable power 126 to operate an electrolysis unit 120 that separates water into hydrogen and oxygen. The electrolysis unit 120 may be coupled to a renewable energy source 125 so as to receive the renewable power 126. The oxygen produced by the electrolysis unit 120 can be fed to the gasification unit 110 via the oxygen product 3, and the hydrogen produced by the electrolysis unit 120 can flow in a hydrogen product 14 that combines with the treated gasification product 12 via a combiner 170 to form an ammonia synthesis feed stream 16.

In aspects, the mole ratio of hydrogen to nitrogen in the ammonia synthesis feed stream 16 can be between about 2:1 to about 4:1, or about 3:1. In further aspects, the mole ratio of hydrogen to nitrogen in the ammonia synthesis feed stream 16 can be between about 2:1 to about 4:1, or about 3:1. The flow of hydrogen in the hydrogen product 14, relative to the flow of the treated gasification product 12, can be controlled such that the mole ratio of hydrogen to nitrogen in the ammonia synthesis feed stream 16 can be between about 2:1 to about 4:1, or about 3:1. In aspects, the treated gasification product 12, the hydrogen product 14, and the ammonia synthesis feed stream 16 can have sensors, control valves, and associated instrumentation configured to measure the amount of hydrogen and nitrogen in one or more of the treated gasification product 12, the hydrogen product 14, and the ammonia synthesis feed stream 16 and to control the flow of hydrogen in the hydrogen product 14 to the combiner 170 such that the process and system 200 control the mole ratio of hydrogen to nitrogen in the ammonia synthesis feed stream 16 to be between about 2:1 to about 4:1, or about 3:1.

The ammonia synthesis feed stream 16 can be fed to an ammonia synthesis unit 180 where an ammonia product 17 may be produced. The ammonia product 17 may be considered green ammonia because the feed to the gasification unit 110 can be biomass 1, air 2, and oxygen product 3 that may be made utilizing renewable power 126. The ammonia synthesis unit 180 can produce steam 18 and a purge gas 19. The steam 18 can be used as steam 7, in some aspects. In some aspects, the purge gas 19 can be used in an auxiliary boiler.

In aspects, the steam 13 that may be removed from the methanation unit 160 can be used in unit 140 for shifting the unshifted syngas. Moreover, the unit 140 can recover a process condensate 6 (aqueous condensate) that can be used as coolant in the heat exchanger 130, the heating of the condensate in the heat exchanger 130 thereby producing steam 15.

In FIG. 2, the green ammonia can be fed to a urea synthesis unit 190, along with cleaned carbon dioxide 20. The cleaned carbon dioxide 20 can be obtained by compressing, purifying, or both compressing and purifying the first portion 11a of the CO2 product 11 in a CO2 treatment unit 195. Put another way, in some aspects the first portion 11a of the CO2 product 11 can be compressed, purified, or both compressed and purified before being fed to the urea synthesis unit 190. Green urea 21a and 21b can be produced by the urea synthesis unit 190, along with reaction product water 22. The reaction product water 22 can have a purity (e.g., <1 ppmw of NH3, CO2, and urea) such that the reaction product water 22 may be passed to a water treatment unit 210 and then can be provided as treated water 23 used in place of fresh water (water 15 in FIG. 1) for feed to the electrolysis unit 120. A fresh water makeup stream (e.g., water 15 in FIG. 1) to the electrolysis unit 120 can be utilized for any water lost in the process and system 200. A portion 21b of the green urea can be fed to a urea formaldehyde synthesis unit 197, along with a green formaldehyde stream 25 (e.g., produced as a derivative of methanol from the process and system 300 in FIG. 3), to produce green urea formaldehyde 24.

The process and system 300 in FIG. 3 can produce methanol and derivatives thereof. The process and system 300 in FIG. 3 can feed a biomass 1 and an oxygen product 3 to a gasification unit 110 to produce an unshifted syngas 4. The unshifted syngas 4 can then be cooled in a heat exchanger 130 to form a cooled syngas 5 and the heating of the condensate in the heat exchanger 130 thereby producing steam 7A, similar to the steam 15 described above. Following cooling, compressing and cleaning the syngas (e.g., to remove sulfur-containing compounds) in a water gas shift unit 145, similar to the water gas shift unit 140 described above, forms a cleaned syngas 8A and a sulfur product 9. The gasification unit 110 may be configured not to receive air and to only receive oxygen from the oxygen product 3 of the electrolysis unit 120; thus, there may be no nitrogen in the cleaned syngas 8A due to the introduction of air to the gasification unit 110, and the cleaned syngas 8A contains hydrogen, carbon monoxide, and carbon dioxide. Carbon dioxide can be separated from the cleaned syngas 8A to produce a CO2 product 11 and a treated gasification product 10A containing carbon monoxide, hydrogen, and residual amounts of carbon dioxide. The CO2 product 11 can be sequestered, stored, or used (e.g., in secondary hydrocarbon recovery).

The process and system 300 in FIG. 3 can use renewable power 126 to operate an electrolysis unit 120 that separates water into hydrogen and oxygen. The electrolysis unit 120 may be coupled to a renewable energy source 125 so as to receive the renewable power 126. The oxygen produced by the electrolysis unit 120 can be fed to the gasification unit 110 via the oxygen product 3, and the hydrogen produced by the electrolysis unit 120 can flow in a hydrogen product 14 that can be combine with the treated gasification product 10A via a combiner 220 to form a synthesis feed stream 101 enriched in hydrogen and containing carbon monoxide, hydrogen, and carbon dioxide.

In aspects, the mole ratio of (H2-CO2)/(CO+CO2) can be between about 1:1 to about 3:1, or about 2:1 in the synthesis feed stream 101. In an embodiment, the mole ratio can be about 2.05:1 in the synthesis feed stream 101. In further aspects, the mole ratio of (H2-CO2)/(CO+CO2) in the synthesis feed stream 101 may be controlled. The flow of hydrogen in the hydrogen product 14, relative to the flow of the treated gasification product 10A, can be controlled such that the mole ratio of (H2-CO2)/(CO+CO2) in the synthesis feed stream 101 can be between about 1:1 to about 3:1, about 2:1, or about 2:05:1. In aspects, the treated gasification product 10A, the hydrogen product 14, and the synthesis feed stream 101 can have sensors, control valves, and associated instrumentation configured to measure the amount of hydrogen, carbon monoxide, carbon dioxide, or a combination thereof in one or more of the treated gasification product 10A, the hydrogen product 14, and the synthesis feed stream 101 and to control the flow of hydrogen in the hydrogen product 14 to the combiner 220 such that the process and system 300 control the mole ratio of (H2-CO2)/(CO+CO2) in the synthesis feed stream 101 to be between about 1:1: to about 3:1, about 2:1, or 2.05:1.

The synthesis feed stream 101 can be fed to a methanol synthesis unit 230 where a methanol product 102 and 104 can be produced. The methanol product 102 and 104 can be considered green methanol because the feed to the gasification unit 110 may be biomass 1 and oxygen product 3 made utilizing renewable power 126. The methanol synthesis unit 230 can produce a purge gas 105 and a reaction water product 103. In some aspects, the purge gas 105 can be used in an auxiliary boiler.

Green methanol 102 and 104 produced in the methanol synthesis unit 230 can have a purity of at least about 95 mol % methanol with the balance being water. Another product of the methanol synthesis can be reaction product water 103 that can optionally be treated in a water treatment unit 210 and then treated water 106, similarly as the treated water 23 as described above, fed to the electrolysis unit 120. The reaction product water 103 can have a purity (e.g., <1 part per million weight (ppmw) of methanol, CO2, and carbon monoxide) such that the reaction product water 103 can be used in place of fresh water (e.g., water 15 in FIG. 1) for feed to the electrolysis unit 120. A fresh water makeup stream (e.g., water 15 in FIG. 1) to the electrolysis unit 120 can be utilized for any water lost in the process and system 300. A portion 102 of the green methanol can be used in a methanol derivatives synthesis unit 240 to produce methanol derivatives 107, such as green formaldehyde, green DME, green gasoline, green acetic acid, green formic acid, green ethanol, green ethylene, green propylene, or combinations thereof.

The process and system 400 produces Fischer Tropsch products and upgraded products thereof. The process and system 400 in FIG. 4 feeds a biomass 1 and an oxygen product 3 to a gasification unit 110 to produce an unshifted syngas 4. The unshifted syngas 4 can then be cooled in a heat exchanger 130 to form a cooled syngas 5 and the heating of the condensate in the heat exchanger 130 thereby producing steam 7A, similar to the steam 15 described above. Following cooling, compressing and cleaning the syngas (e.g., to remove sulfur-containing compounds) in a water gas shift unit 145, similar to the water gas shift unit 140 described above, forms a cleaned syngas 8A and a sulfur product 9. The gasification unit 110 may be configured not to receive air and to only receive oxygen from the oxygen product 3 of the electrolysis unit 120; thus, there may be no nitrogen in the cleaned syngas 8A due to the introduction of air to the gasification unit 110, and the cleaned syngas 8A can include hydrogen, carbon monoxide, and carbon dioxide. Carbon dioxide can be separated from the cleaned syngas 8A to produce a CO2 product 11 and a treated gasification product 10A containing carbon monoxide, hydrogen, and residual amounts of carbon dioxide. The CO2 product 11 can be sequestered, stored, or used (e.g., in secondary hydrocarbon recovery).

The process and system 400 in FIG. 4 uses renewable power 126 to operate an electrolysis unit 120 that can separate water into hydrogen and oxygen. The electrolysis unit 120 can be coupled to a renewable energy source 125 so as to receive the renewable power 126. The oxygen produced by the electrolysis unit 120 can be fed to the gasification unit 110 via the oxygen product 3, and the hydrogen produced by the electrolysis unit 120 can flow in a hydrogen product 14. The hydrogen product 14 may be split into a first portion 14a and a second portion 14b via a splitter 270. A first portion 14a of the hydrogen product 14 can be combined with the treated gasification product 10A via a combiner 220 to form a synthesis feed stream 101 that may be enriched in hydrogen and may contain carbon monoxide, hydrogen, and carbon dioxide. A second portion 14b of the hydrogen product 14 can be used for upgrading Fischer Tropsch product (described in more detail below).

In aspects, the mole ratio of (H2-CO2)/(CO+CO2) is about 2:1 in the synthesis feed stream 101. In an embodiment, the mole ratio is about 2.05:1 in the synthesis feed stream 101. In further aspects, the mole ratio of (H2-CO2)/(CO+CO2) in the synthesis feed stream 101 may be controlled. The flow of hydrogen in first portion 14a of the hydrogen product 14, relative to the flow of the treated gasification product 10A, can be controlled such that the mole ratio of (H2-CO2)/(CO+CO2) in the synthesis feed stream 101 may be about 2:1, or about 2:05:1. In aspects, the treated gasification product 10A, the hydrogen product 14, and the synthesis feed stream 101 can have sensors, control valves, and associated instrumentation configured to measure the amount of hydrogen, carbon monoxide, carbon dioxide, or a combination thereof in one or more of the treated gasification product 10A, the hydrogen product 14, and the synthesis feed stream 101 and to control the flow of hydrogen in the hydrogen product 14 to the combiner 220 such that the process and system 400 control the mole ratio of (H2-CO2)/(CO+CO2) in the synthesis feed stream 101 to be about 2:1, or about 2.05:1.

The synthesis feed stream 101 can be fed to a Fischer Tropsch (FT) synthesis unit 250 where a Fischer Tropsch (FT) product 112 containing long chain hydrocarbons may be produced. The FT product 112 can be considered a green FT product because the feed to the gasification unit 110 can be biomass 1 and oxygen product 3 that may be made utilizing renewable power 126. The FT synthesis unit 250 can produce a tail gas 111, a wax 116, and a reaction water product 113. The reaction water product 113 can be fed to a water treatment unit 210, which may provide a treated water 114 to the electrolyzer 120, similarly as described above. In some aspects, the tail gas 111 can be used in an auxiliary boiler.

Long chain hydrocarbons in the FT product 112 along with wax 116 formed in the FT synthesis unit 250 and the second portion 14b of the hydrogen product 14 can be used to made green FT derivative products 115 in a FT product upgrading unit 260. The derivative products 115 can include green LPG, green naphtha, green jet fuel, green diesel, green wax, green lubricants, or a combination thereof. In some aspects, some of the derivatives 115 can be used as fuel for the gasification unit 110.

Having described various systems and methods herein, certain aspects and advantages of the discloses process and apparatus can include:

In a first aspect, a process comprises: producing an unshifted syngas from biomass and oxygen in a gasification unit; introducing water into an electrolyzer to produce an oxygen product and a hydrogen product, wherein the electrolyzer may be powered by renewable energy; and introducing the oxygen product to the gasification unit, wherein the oxygen product supplies at least a portion of the oxygen to the gasification unit.

A second aspect can include the process of the first aspect, further comprises: introducing air to the gasification unit, wherein the air supplies at least a portion of the oxygen to the gasification unit; cooling the unshifted syngas to form a cooled syngas; introducing the cooled syngas to a water gas shift unit to produce a shifted syngas; removing sulfur from the shifted syngas to produce sulfur depleted syngas and sulfur product; removing CO2 from the sulfur depleted syngas to produce a CO2 depleted syngas and a CO2 product; introducing the CO2 depleted syngas to a methanation unit to produce a methanation product to produce a treated gasification product comprising nitrogen and hydrogen; and combining the treated gasification product and the hydrogen product to form an ammonia synthesis feed stream having a mole ratio of hydrogen to nitrogen of 3:1.

A third aspect can include the process of the first or second aspect, further comprises: introducing the ammonia synthesis feed stream to an ammonia synthesis unit to produce an ammonia product.

A fourth aspect can include the process of any of the first to third aspects, further comprises: introducing the ammonia product and a CO2 feed stream to a urea synthesis unit to produce a urea product and a water product.

A fifth aspect can include the process of any of the first to fourth aspects, further comprises: compressing and purifying the CO2 product to produce the CO2 feed stream.

A sixth aspect can include the process of any of the first to fifth aspects, further comprises:
introducing the water product to the electrolyzer, wherein the water product may be the water that may be introduced to the electrolyzer, wherein the water product may be optionally treated before introducing the water product to the electrolyzer.

A seventh aspect can include the process of any of the first to sixth aspects, further comprises: introducing a portion of the urea product and a formaldehyde feed to a urea formaldehyde synthesis unit to produce a urea formaldehyde product.

An eighth aspect can include the process of any of the first to seventh aspects, further comprises: cooling the unshifted syngas to form a cooled syngas; removing sulfur from the cooled syngas to produce sulfur depleted syngas and a sulfur product; removing CO2 from the sulfur depleted syngas to produce a treated gasification product and a CO2 product;

and combining the treated gasification product and at least a portion of the hydrogen product to form a synthesis feed stream that satisfies the following: [moles H2-moles CO2]/[moles CO+moles CO2]=2.05.

A ninth aspect can include the process of any of the first to eighth aspects, wherein a mole ratio of hydrogen to carbon monoxide in the treated gasification product is about 1:1.

A tenth aspect can include the process of any of the first to ninth aspects, wherein the treated gasification product is combined with all of the hydrogen product, the process further comprising: introducing the synthesis feed stream to a methanol synthesis unit to produce a methanol product and a water product.

An eleventh aspect can include the process of any of the first to tenth aspects, further comprises: introducing the water product to the electrolyzer, wherein the water product is the water that is introduced to the electrolyzer.

A twelfth aspect can include the process of any of the first to eleventh aspects, further comprises: introducing a portion of the methanol product to a derivatives synthesis unit to produce formaldehyde, dimethyl ether (DME), gasoline, acetic acid, formic acid, ethanol, ethylene, propylene, or a combination thereof.

A thirteenth aspect can include the process of any of the first to twelfth aspects, further comprises: splitting the hydrogen product into a first portion and a second portion, wherein the treated gasification product is combined with the first portion of the hydrogen product to form the synthesis feed stream; and introducing the synthesis feed stream to a Fischer Tropsch (FT) synthesis unit to produce a FT product, a wax product, and a water product.

A fourteenth aspect can include the process of any of the first to thirteenth aspects, further comprises: introducing the water product to the electrolyzer, wherein the water product is the water that is introduced to the electrolyzer, wherein the water product is optionally treated before introducing the water product to the electrolyzer.

A fifteenth aspect can include the process of any of the first to fourteenth aspects, further comprises: introducing the second portion of the hydrogen product, the wax product, and the FT product to a derivative synthesis unit to produce naphtha, jet fuel, diesel, wax, lubricant, or a combination thereof.

In a sixteenth aspect, a system comprises: a gasification unit configured to produce an unshifted syngas from biomass and oxygen; and an electrolyzer coupled to the gasification unit and configured to receive water and to produce an oxygen product and a hydrogen product, wherein the oxygen product supplies at least a portion of the oxygen to the gasification unit, and wherein the electrolyzer is coupled to a renewable energy source.

A seventeenth aspect can include a system of the sixteenth aspect, further comprises: an air stream connected to the gasification unit and configured to supply air to the gasification unit, wherein the air supplies at least a portion of the oxygen to the gasification unit; a heat exchanger coupled to the gasification unit and configured to cool the unshifted syngas to produce a cooled syngas; a water gas shift unit coupled to the heat exchanger and configured to receive the cooled syngas and to produce a shifted syngas; a sulfur removal unit coupled to the water gas shift unit and configured to receive the shifted syngas and to produce a sulfur depleted syngas and a sulfur product; an absorption unit coupled to the sulfur removal unit and configured to receive the sulfur depleted syngas, remove carbon dioxide from the sulfur depleted syngas, and produce a CO2 depleted syngas and a CO2 product; a methanation unit coupled to the absorption unit and configured to receive the CO2 depleted syngas to produce a treated gasification product comprising hydrogen and nitrogen; and a combiner configured to receive the treated gasification product and the hydrogen product and to produce an ammonia synthesis feed stream having a mole ratio of hydrogen to nitrogen of about 3:1.

An eighteenth aspect can include a system of the sixteenth or seventeenth aspect, further comprises: an ammonia synthesis unit coupled to the combiner and configured to receive the ammonia synthesis feed stream from the combiner and to produce an ammonia product.

A nineteenth aspect can include a system of any of the sixteenth to eighteenth aspects, further comprises: a urea synthesis unit coupled to the ammonia synthesis unit and configured to receive the ammonia product and a CO2 feed stream and to produce a urea product and a water product.

A twentieth aspect can include a system of any of the sixteenth to nineteenth aspects, further comprises: a CO2 treatment unit coupled to the absorption unit and to the urea synthesis unit and configured to receive the CO2 product from the absorption unit and to produce the CO2 feed stream.

A twenty first aspect can include a system of any of the sixteenth to twentieth aspects, wherein the urea synthesis unit is coupled to the electrolyzer, and wherein the electrolyzer is configured to receive the water product.

A twenty second aspect can include a system of any of the sixteenth to twenty first aspects, further comprises: a urea formaldehyde synthesis unit coupled to the urea synthesis unit and configured to receive at portion of the urea product from the urea synthesis unit and to produce a urea formaldehyde produce.

A twenty third aspect can include a system of any of the sixteenth to twenty second aspects, wherein the gasification unit is configured to receive the oxygen product as the only source of oxygen that is fed to the gasification unit.

A twenty fourth aspect can include a system of any of the sixteenth to twenty third aspects, further comprises: a heat exchanger coupled to the gasification unit and configured to cool the unshifted syngas to produce a cooled syngas; a sulfur removal unit coupled to the heat exchanger and configured to receive the unshifted syngas and to produce a sulfur depleted syngas and a sulfur product; an absorption unit coupled to the sulfur removal unit and configured to receive the sulfur depleted syngas, remove carbon dioxide from the sulfur depleted syngas, and produce a treated gasification product and a CO2 product; and a combiner configured to receive the treated gasification product and at least a portion of the hydrogen product and to produce a synthesis feed stream that satisfies the following: [moles H2-moles CO2]/[moles CO+moles CO2]=2.05.

A twenty fifth aspect can include a system of any of the sixteenth to twenty fourth aspects, wherein the combiner is configured to receive all of the hydrogen product to produce the synthesis feed stream, the system further comprises: a methanol synthesis unit coupled to the combiner and configured to receive the synthesis feed stream and to produce a methanol product and a water product.

A twenty sixth aspect can include a system of any of the sixteenth to twenty fifth aspects, further comprises: a derivatives synthesis unit coupled to the methanol synthesis unit and configured to receive the methanol product and to produce formaldehyde, dimethyl ether (DME), gasoline, acetic acid, formic acid, ethanol, ethylene, propylene, or a combination thereof.

A twenty seventh aspect can include a system of any of the sixteenth to twenty sixth aspects, wherein the methanol synthesis unit is coupled to the electrolyzer, optionally via a water treatment unit, and the electrolyzer is configured to receive the water product.

A twenty eighth aspect can include a system of any of the sixteenth to twenty seventh aspects, further comprises: a splitter coupled to the electrolyzer and configured to split the hydrogen product into a first portion and a second portion, wherein the combiner is coupled to the splitter and configured to receive the first portion of the hydrogen product to form the synthesis feed stream; and a Fischer Tropsch (FT) synthesis unit coupled to the combiner and configured to receive the synthesis feed stream and to produce a FT product, a wax product, and a water product.

A twenty ninth aspect can include a system of any of the sixteenth to twenty eighth aspects, further comprises: a FT product unit coupled to the FT synthesis unit and to the splitter and configured to receive the second portion of the hydrogen product, the wax product, and the FT product and to produce naphtha, jet fuel, diesel, wax, lubricant, or a combination thereof.

A thirtieth aspect can include a system of any of the sixteenth to twenty ninth aspects, wherein the FT synthesis unit is coupled to the electrolyzer, optionally via a water treatment unit, and the electrolyzer is configured to receive the water product.

While various embodiments have been shown and described, modifications thereof can be made by one skilled in the art without departing from the spirit and teachings of the disclosure. The embodiments described herein are exemplary only, and are not intended to be limiting. Many variations and modifications of the subject matter disclosed herein are possible and are within the scope of the disclosure. Where numerical ranges or limitations are expressly stated, such express ranges or limitations should be understood to include iterative ranges or limitations of like magnitude falling within the expressly stated ranges or limitations (e.g., from about 1 to about 10 includes, 2, 3, 4, etc.; greater than 0.10 includes 0.11, 0.12, 0.13, etc.). For example, whenever a numerical range with a lower limit, RL and an upper limit, RU is disclosed, any number falling within the range is specifically disclosed. In particular, the following numbers within the range are specifically disclosed: R=RL+k*(RU−RL), wherein k is a variable ranging from 1 percent to 100 percent with a 1 percent increment, i.e., k is 1 percent, 2 percent, 3 percent, 4 percent, 5 percent, . . . 50 percent, 51 percent, 52 percent, 90, 95 percent, 96 percent, 97 percent, 98 percent, 99 percent, or 100 percent. Moreover, any numerical range defined by two R numbers as defined in the above is also specifically disclosed. Use of the term "optionally" with respect to any element of a claim is intended to mean that the subject element is required, or alternatively, is not required. Both alternatives are intended to be within the scope of the claim. Use of broader terms such as comprises, includes, having, etc. should be understood to provide support for narrower terms such as consisting of, consisting essentially of, comprised substantially of, etc.

Accordingly, the scope of protection is not limited by the description set out above but is only limited by the claims which follow, that scope including all equivalents of the subject matter of the claims. Each and every claim is incorporated into the specification as an embodiment of the present disclosure. Thus, the claims are a further description and are an addition to the embodiments of the present disclosure. The discussion of a reference is not an admission that it is prior art to the present disclosure, especially any reference that may have a publication date after the priority date of this application. The disclosures of all patents, patent applications, and publications cited herein are hereby incorporated by reference, to the extent that they provide exemplary, procedural, or other details supplementary to those set forth herein.

What is claimed is:

1. A system comprising:
   a gasification unit configured to produce an unshifted syngas from biomass and oxygen;
   an electrolyzer coupled to the gasification unit and configured to receive water and to produce an oxygen product and a hydrogen product;
   an air stream connected to the gasification unit and configured to supply air to the gasification unit, wherein the air stream supplies at least a portion of oxygen to the gasification unit;
   a heat exchanger coupled to the gasification unit and configured to cool the unshifted syngas to produce a cooled syngas;
   a water gas shift unit coupled to the heat exchanger and configured to receive the cooled syngas and to produce a shifted syngas;
   a sulfur removal unit coupled to the water gas shift unit and configured to receive the shifted syngas and to produce a sulfur depleted syngas and a sulfur product;
   an absorption unit coupled to the sulfur removal unit and configured to receive the sulfur depleted syngas, remove carbon dioxide from the sulfur depleted syngas, and produce a $CO_2$ depleted syngas and a $CO_2$ product;
   a methanation unit coupled to the absorption unit and configured to receive the $CO_2$ depleted syngas to produce a treated gasification product comprising hydrogen and nitrogen; and
   a combiner configured to receive the treated gasification product and the hydrogen product and to produce an ammonia synthesis feed stream having a mole ratio of hydrogen to nitrogen of about 3:1,
   wherein the oxygen product supplies at least a portion of the oxygen to the gasification unit, and
   wherein the electrolyzer is coupled to a renewable energy source.

2. The system of claim 1, further comprising:
   an ammonia synthesizer coupled to the combiner and configured to receive the ammonia synthesis feed stream from the combiner and to produce an ammonia product.

3. The system of claim 2, further comprising:
   a urea synthesizer coupled to the ammonia synthesizer and configured to receive the ammonia product and a $CO_2$ feed stream and to produce a urea product and a water product.

4. The system of claim 3, further comprising:
   a $CO_2$ treatment unit coupled to the absorption unit and to the urea synthesizer and configured to receive the $CO_2$ product from the absorption unit and to produce the $CO_2$ feed stream.

5. The system of claim 1, further comprising:
   the sulfur removal unit coupled to the heat exchanger and configured to receive the unshifted syngas and to produce the sulfur depleted syngas and the sulfur product;
   an absorption unit coupled to the sulfur removal unit and configured to receive the sulfur depleted syngas, remove carbon dioxide from the sulfur depleted syngas, and produce the treated gasification product and a $CO_2$ product; and the combiner configured to receive the treated gasification product and at least a portion of the hydrogen product and to produce a synthesis feed stream that satisfies the following: [moles $H_2$−moles $CO_2$]/[moles CO+moles $CO_2$]=2.05.

6. The system of claim 5, wherein the combiner is configured to receive all of the hydrogen product to produce the synthesis feed stream, the system further comprising:

a methanol synthesizer coupled to the combiner and configured to receive the synthesis feed stream and to produce a methanol product and a water product; and a derivatives synthesizer coupled to the methanol synthesizer and configured to receive the methanol product and to produce formaldehyde, dimethyl ether (DME), gasoline, acetic acid, formic acid, ethanol, ethylene, propylene, or a combination thereof.

7. The system of claim 6, further comprising:

a splitter coupled to the electrolyzer and configured to split the hydrogen product into a first portion and a second portion, wherein the combiner is coupled to the splitter and configured to receive the first portion of the hydrogen product to form the synthesis feed stream; and a Fischer Tropsch (FT) synthesizer coupled to the combiner and configured to receive the synthesis feed stream and to produce a FT product, a wax product, and a water product.

8. A system comprising:

a gasification unit configured to produce an unshifted syngas from biomass and oxygen;

an electrolyzer coupled to the gasification unit and configured to receive water and to produce an oxygen product and a hydrogen product;

a heat exchanger coupled to the gasification unit and configured to cool the unshifted syngas to produce a cooled syngas;

a sulfur removal unit coupled to the heat exchanger and configured to receive the unshifted syngas and to produce a sulfur depleted syngas and a sulfur product;

an absorption unit coupled to the sulfur removal unit and configured to receive the sulfur depleted syngas, remove carbon dioxide from the sulfur depleted syngas, and produce a treated gasification product and a $CO_2$ product; and a combiner configured to receive the treated gasification product and at least a portion of the hydrogen product and to produce a synthesis feed stream that satisfies the following: [moles $H_2$−moles $CO_2$]/[moles CO+moles $CO_2$]=2.05, wherein the oxygen product supplies at least a portion of the oxygen to the gasification unit, and wherein the electrolyzer is coupled to a renewable energy source.

9. The system of claim 8, wherein the combiner is configured to receive all of the hydrogen product to produce the synthesis feed stream, the system further comprising:

a methanol synthesizer coupled to the combiner and configured to receive the synthesis feed stream and to produce a methanol product and a water product; and a derivatives synthesizer coupled to the methanol synthesizer and configured to receive the methanol product and to produce formaldehyde, dimethyl ether (DME), gasoline, acetic acid, formic acid, ethanol, ethylene, propylene, or a combination thereof.

10. The system of claim 9, further comprising:

a splitter coupled to the electrolyzer and configured to split the hydrogen product into a first portion and a second portion, wherein the combiner is coupled to the splitter and configured to receive the first portion of the hydrogen product to form the synthesis feed stream; and a Fischer Tropsch (FT) synthesizer coupled to the combiner and configured to receive the synthesis feed stream and to produce a FT product, a wax product, and another water product.

11. The system of claim 8, further comprising:

an ammonia synthesizer coupled to the combiner and configured to receive an ammonia synthesis feed stream from the combiner and to produce an ammonia product.

12. The system of claim 11, further comprising:

a urea synthesizer coupled to the ammonia synthesizer and configured to receive the ammonia product and a $CO_2$ feed stream and to produce a urea product and a water product.

13. The system of claim 12, further comprising:

a $CO_2$ treatment unit coupled to the absorption unit and to the urea synthesizer unit and configured to receive the $CO_2$ product from the absorption unit and to produce the $CO_2$ feed stream.

14. The system of claim 3, further comprising:

a urea-formaldehyde synthesizer coupled to the urea synthesizer and configured to receive at least a portion of the urea product from the urea synthesizer and to produce a urea formaldehyde produce.

15. The system of claim 12, further comprising:

a urea-formaldehyde synthesizer coupled to the urea synthesizer and configured to receive at least a portion of the urea product from the urea synthesizer and to produce a urea formaldehyde produce.

16. The system of claim 1, wherein the mole ratio of hydrogen to carbon monoxide in the treated gasification product is about 1:1.

17. The system of claim 6, wherein the water product is introduced to the electrolyzer, and the water product is the water that is introduced to the electrolyzer.

18. The system of claim 7, wherein the water product is introduced to the electrolyzer, and the water product is the water that is introduced to the electrolyzer.

19. The system of claim 9, wherein the water product is introduced to the electrolyzer, and the water product is the water that is introduced to the electrolyzer.

20. The system of claim 10, wherein the water product is introduced to the electrolyzer, and the water product is the water that is introduced to the electrolyzer.

* * * * *